US006780220B2

(12) United States Patent
Milbrath et al.

(10) Patent No.: US 6,780,220 B2
(45) Date of Patent: Aug. 24, 2004

(54) METHOD FOR GENERATING POLLUTION CREDITS WHILE PROCESSING REACTIVE METALS

(75) Inventors: Dean S. Milbrath, West Lakeland Township, MN (US); John G. Owens, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 40 days.

(21) Appl. No.: 10/394,853

(22) Filed: Mar. 22, 2003

(65) Prior Publication Data

US 2003/0164069 A1 Sep. 4, 2003

Related U.S. Application Data

(63) Continuation-in-part of application No. 09/780,256, filed on Feb. 9, 2001, now Pat. No. 6,537,346.
(60) Provisional application No. 60/202,169, filed on May 4, 2000.

(51) Int. Cl.[7] .............................................. C22B 26/22
(52) U.S. Cl. ............................ 75/602; 75/709; 705/1
(58) Field of Search ........................ 75/602, 709; 705/1

(56) References Cited

U.S. PATENT DOCUMENTS

| | | |
|---|---|---|
| 1,972,317 A | 9/1934 | Reimers |
| 3,185,734 A | 5/1965 | Fawcett et al. |
| 4,136,121 A | 1/1979 | Martini et al. |
| 4,173,538 A | 11/1979 | Herbline |
| 4,457,775 A | 7/1984 | Legge et al. |
| 4,659,377 A | 4/1987 | Foerster |
| 4,770,697 A | 9/1988 | Zurecki |
| 5,040,609 A | 8/1991 | Dougherty, Jr. et al. |
| 5,084,190 A | 1/1992 | Fernandez |
| 5,115,868 A | 5/1992 | Dougherty, Jr. et al. |
| 5,117,917 A | 6/1992 | Robin et al. |
| 5,124,053 A | 6/1992 | Iikubo et al. |
| 5,141,654 A | 8/1992 | Fernandez |
| 5,247,101 A | 9/1993 | Takago et al. |
| 5,250,200 A | 10/1993 | Sallet |
| 5,399,718 A | 3/1995 | Costello et al. |
| 5,444,102 A | 8/1995 | Nimitz et al. |
| 5,457,238 A | 10/1995 | Petrov et al. |
| 5,466,877 A | 11/1995 | Moore |
| 5,476,974 A | 12/1995 | Moore et al. |
| 5,488,142 A | 1/1996 | Fall et al. |
| 5,718,293 A | 2/1998 | Flynn et al. |
| 5,855,647 A | 1/1999 | Li et al. |
| 5,998,671 A | 12/1999 | Van Der Puy |
| 6,398,844 B1 | 6/2002 | Hobbs et al. |
| 6,478,979 B1 | 11/2002 | Rivers et al. |
| 6,521,018 B2 | 2/2003 | Hobbs et al. |
| 6,537,346 B2 | 3/2003 | Milbrath et al. |
| 6,601,033 B1 * | 7/2003 | Sowinski ...................... 705/1 |
| 2001/0027702 A1 | 10/2001 | Hobbs et al. |

FOREIGN PATENT DOCUMENTS

| | | |
|---|---|---|
| DE | 197 47 002 | 4/1999 |
| EP | 1 122 322 | 8/2001 |
| GB | 1 192 238 | 5/1970 |
| JP | 5214384 | 8/1993 |
| JP | 10231499 | 9/1998 |
| JP | 2869432 | 1/1999 |
| JP | 2893038 | 5/1999 |
| SU | 698289 | 2/1985 |
| WO | WO 96/22129 | 7/1996 |
| WO | WO 98/19742 | 5/1998 |
| WO | WO 00/64614 | 11/2000 |
| WO | WO 01/05468 | 1/2001 |

OTHER PUBLICATIONS

J.H. Simons, Fluorine Chemistry, vol. 1, pp. 432–433, 1950, Publishers, Academic Press Inc., New York, NY.

J.W. Fruehling and J.D. Hanawalt, "Protective Atmospheres for Melting Magnesium Alloys," Transactions of the American Foundrymen's Society, vol. 77, pp. 159–164, 1969.

H. Gjestland, Norsk Hydro, Research Centre Porsgrunn, D. Magers, Hydro Magnesium, Progress to Eliminate $SF_8$ as a Protective Gas in Magnesium Diecasting, no date, Brussels.

Scientific Assessment of Ozone Depletion, World Meteorological Organization Global Ozone Research and Monitoring Project—Report 44, Chapter 10, pp. 10.1–10.30, 1998.

The Montreal Protoool on Substances that Deplete the Ozone Layer, United Nations Environment Programme (UNEP), Sections 2.1, 2.2, 1987, Nairobi, Kenya.

Kyoto Protocol to the United Nations Framework Convention on Climate Change, United Nations Environment Programme (UNEP), pp. 1–23, 1997, Nairobi, Kenya.

John H. Seinfeld and Spyros N. Pandis, Atmospheric Chemistry and Physics: From Air Pollution to Climate Change, pp. 212–215, and 288–289, 1998, John Wiley & Sons, Inc., New York.

Schemm, G., "Schwefelhexafluorid als Oxydationsschutz fur Magnesiumschmelzen" Giesserei, Giesserei Verlag, vol. 58, No. 19, pp. 558–565, Sep. 23, 1971, XP002085525.

P.S. Zurer, "Looming Ban on Production of CFCs, Halons Spurs Switch to Substitutes," Chemical & Engineering News, pp. 12–18, Nov. 15, 1993.

S.O. Andersen et al., "Halons Stratospheric Ozone and the U.S. Air Force," The Military Engineer, vol. 80, No. 523, pp 485–492, Aug. 1988.

US Navy Halon 1211 Replacement Plan Part 1–Development of Halon 1211 Alternatives, pp. 1–67, Nov. 1, 1999, Naval Research Lab, Washington, D.C.

(List continued on next page.)

Primary Examiner—Melvyn J. Andrews

(57) ABSTRACT

This invention relates to a method for generating pollution credits while processing molten magnesium, aluminum, lithium, and alloys of such metals by contacting the molten metal or alloy with a gaseous mixture comprising a fluorocarbon selected from the group consisting of perfluoroketones, hydrofluoroketones, and mixtures thereof.

9 Claims, No Drawings

OTHER PUBLICATIONS

R.D. Smith et al., "The Chemistry of Carbonyl Fluoride II. Synthesis of Perfluoroisopropyl Ketones," Journal of American Chemical Society, v. 84, pp. 4285–4288, 1962.

ASTM E681–1998 (update of E681–85) Standard Test Method for Concentration Limits of Flammability of Chemicals (Vapors and Gases) 1998.

NFPA 2001, "Standard for Clean Agent Fire Extinguishing Systems," 2000 Edition, Table 1–5.1.2, pp. 2001–5, 2000.

Chemical Abstracts, vol. 82, Apr. 14–Apr. 28 (Abstracts 92724–112252), p. 406, published by the American Chemical Society 1975.

Marchionni, G. et al., "Hydrofluoropolyethers" *Journal of Fluorine Chemistry*, 95, 41–50, 1999.

Martinez, R.D., et al., "The Near U.V. Absorption Spectra of Several Aliphatic Aldehydes and Ketones at 300 K", Atmospheric Environment, 26, 785–792, 1992.

Pinnock, et al., Radiative Forcing of Climate by Hydrochlorofluorocarbons and Hydrofluorocarbons, Journal of Geophysical Research, No. D11, 23,227–23,238, 1995.

* cited by examiner

US 6,780,220 B2

METHOD FOR GENERATING POLLUTION CREDITS WHILE PROCESSING REACTIVE METALS

CROSS-REFERENCE TO RELATED APPLICATION

This application is a continuation-in-part of U.S. patent application Ser. No. 09/780,256, filed Feb. 9, 2001, and now U.S. Pat. No. 6,537,346, and claims priority to U.S. Provisional Patent Application No. 60/202,169, filed May 4, 2000, each of which is incorporated herein by reference in its entirety.

FIELD OF THE INVENTION

This invention relates in one aspect to a method for generating pollution credits while processing molten reactive metals such as magnesium, aluminum, lithium, and alloys of such metals.

BACKGROUND OF THE INVENTION

Molded parts made of magnesium (or its alloys) are finding increasing use as components in the automotive and aerospace industries. These parts are typically manufactured in a foundry, where the magnesium is heated to a molten state to a temperature as high as 1400° F. (800° C.), and the resulting molten magnesium is poured into molds or dies to form ingots or castings. During this casting process, protection of the magnesium from atmospheric air is essential to prevent a spontaneous exothermic reaction from occurring between the reactive metal and the oxygen in the air. Protection from air is also necessary to minimize the propensity of reactive magnesium vapors to sublime from the molten metal bath to cooler portions of a casting apparatus. In either situation, an extremely hot magnesium fire can result within a few seconds of air exposure, potentially causing extensive property damage and serious injury or loss of human life. Similarly, aluminum, lithium, and alloys of such metals are highly reactive in molten form necessitating protection from atmospheric air.

Various methods have been investigated to minimize the exposure of molten magnesium to air. See J. W. Fruehling et al., *Transactions of the American Foundry Society, Proceeding of the 73$^{rd}$ Annual Meeting*, May 5–9, 1969, 77 (1969). The two most viable methods for effectively separating molten magnesium from air are the use of salt fluxes and the use of cover gases (sometimes referred to as "protective atmospheres"). A salt flux is fluid at the magnesium melt temperature and it effectively forms a thin impervious film on the surface of the magnesium, thus preventing the magnesium from reacting with oxygen in the air. However, the use of salt fluxes presents several disadvantages. First, the flux film itself can oxidize in the atmosphere to harden into a thick deposit of complex metal oxide/chlorides, which is easily cracked to expose molten magnesium to the atmosphere. Second, the salt fluxes are typically hygroscopic and, as such, can form salt inclusions in the metal surface which can lead to corrosion. Third, fumes and dust particles from fluxes can cause serious corrosion problems to ferrous metals in the foundry. Fourth, salt sludge can form in the bottom of the crucible. Fifth, and not least, removal of such fluxes from the surface of cast magnesium parts can be difficult.

As a result, there has been a shift from using salt fluxes to using cover gases to inert molten magnesium. Cover gases can be described as one of two types: inert cover gases and reactive cover gases. Inert cover gases can be non-reactive (e.g., argon or helium) or slowly reactive (e.g., nitrogen, which reacts slowly with molten magnesium to form $Mg_3N_2$). For inert cover gases to be effective, air must be essentially excluded to minimize the possibility of metal ignition, i.e., the system must be essentially closed. To utilize such a closed system, workers either have to be equipped with a cumbersome self-contained breathing apparatus or they have to be located outside of the dimensions of the processing area (e.g., by using remote control). Another limitation of inert cover gases is that they are incapable of preventing molten metal from subliming.

Reactive cover gases are gases used at low concentration in a carrier gas, normally ambient air, that react with the molten magnesium at its surface to produce a nearly invisible, thermodynamically stable film. By forming such a tight film, the aerial oxygen is effectively separated from the surface of the molten magnesium, thus preventing metal ignition and minimizing metal sublimation.

The use of various reactive cover gases to protect molten magnesium from ignition has been investigated as early as the late 1920s. An atmosphere containing $CO_2$ is innocuous and economical yet forms a protective film on a magnesium surface which can prevent ignition for over 1 hour at 650° C. However, the $CO_2$-based films formed are dull in appearance and unstable, especially in the presence of high levels of air, and consequently offer little protection for the magnesium surface from ambient oxygen. In effect, the $CO_2$ behaves more like an inert cover gas than a reactive cover gas.

U.S. Pat. No. 4,770,697 (Zurecki) discloses the use of dichlorodifluoromethane as a blanketing atmosphere or cover gas for molten aluminum-lithium alloys. U.S. Pat. Nos. 6,398,844 and 6,521,018 (both Hobbs et al.) disclose blanketing gases used with non-ferrous metals and alloys with reduced Global Warming Potentials, but which are very toxic to workers and/or corrosive to process equipment.

$SO_2$ has been investigated in the past as a reactive cover gas, as $SO_2$ reacts with molten magnesium to form a thin, nearly invisible film of magnesium oxysulfides. $SO_2$ is low in cost and is effective at levels of less than 1% in air in protecting molten magnesium from ignition. However, $SO_2$ is very toxic and consequently requires significant measures to protect workers from exposure (permissible exposure levels are only 2 ppm by volume or 5 mg/m$^3$ by volume). Another problem with $SO_2$ is its reactivity with water in humid air to produce very corrosive acids ($H_2SO_4$ and $H_2SO_3$). These acids can attack unprotected workers and casting equipment, and they also contribute significantly to acid rain pollution when vented out of the foundry. $SO_2$ also has a tendency to form reactive deposits with magnesium which produce metal eruptions from the furnace (especially when $SO_2$ concentrations in the air are allowed to drift too high). Though $SO_2$ has been used commercially on a large scale for the casting of magnesium alloys, these drawbacks have led some manufacturers to ban its use.

Fluorine-containing reactive cover gases provide an inert atmosphere which is normally very stable to chemical and thermal breakdown. However, such normally stable gases will decompose upon contact with a molten magnesium surface to form a thin, thermodynamically stable magnesium oxide/fluoride protective film. U.S. Pat. No. 1,972,317 (Reimers et. al.) describes the use of fluorine-containing compounds which boil, sublime or decompose at temperatures below about 750° C. to produce a fluorine-containing atmosphere which inhibits the oxidation of molten magnesium. Suitable compounds listed include gases, liquids or solids such as $BF_3$, $NF_3$, $SiF_4$, $PF_5$, $SF_6$, $SO_2F_2$, $(CClF_2)_2$, HF, $NH_4F$ and $NH_4PF_6$. The use of $BF_3$, $SF_6$, $CF_4$ and $(CClF_2)_2$ as fluorine-containing reactive cover gases is disclosed in J. W. Fruehling et al., described supra.

Each of these fluorine-containing compounds has one or more deficiencies. Though used commercially and effectively at lower levels than $SO_2$, $BF_3$ is toxic and corrosive and can be potentially explosive with molten magnesium. $NF_3$, $SiF_4$, $PF_5$, $SO_2F_2$ and HF are also toxic and corrosive. $NH_4F$ and $NH_4PF_6$ are solids which sublime upon heating to form toxic and corrosive vapors. $CF_4$ has a very long atmospheric lifetime. $(CClF_2)_2$, a chlorofluorocarbon, has a very high ozone depletion potential (ODP). The ODP of a compound is usually defined as the total steady-state ozone destruction, vertically integrated over the stratosphere, resulting from the unit mass emission of that compound relative to that for a unit mass emission of CFC-11 ($CCl_3F$). See Seinfeld, J. H. and S. N. Pandis, *Atmospheric Chemistry and Physics: From Air Pollution to Climate Change,* John Wiley & Sons, Inc., New York, (1998). Currently, there are efforts underway to phase out the production of substances that have high ODPs, including chlorofluorocarbons and HCFCs, in accordance with the Montreal Protocol. *UNEP (United Nations Environment Programme),* Montreal Protocol on Substances that Deplete the Ozone Layer and its attendant amendments, Nairobi, Kenya, (1987).

Until recently, $SF_6$ was considered the optimum reactive cover gas for magnesium. $SF_6$ is effective yet safe (essentially inert, odorless, low in toxicity, nonflammable and not corrosive to equipment). It can be used effectively at low concentrations either in air (<1%) or in $CO_2$ to form a very thin film of magnesium oxyfluorides and oxysulfides on the surface of molten magnesium. This magnesium oxide/fluoride/sulfide/sulfur oxide film is far superior at protecting the magnesium from a vigorous exothermic oxidation reaction than is the magnesium oxide film inherently present on the metal surface. The magnesium oxide/fluoride/sulfide/sulfur oxide film is sufficiently thin (i.e., nearly invisible to the naked eye) that the metal surface appears to be metallic. This superior protection is believed to result from the greater thermodynamic stability of a nonporous magnesium sulfide/sulfur oxide and/or magnesium oxide/fluoride film as compared to the stability of a thick porous film of either magnesium oxide, sulfide or fluoride alone.

In a typical molten magnesium process employing a reactive cover gas, only a small portion of the gas passed over the molten magnesium is actually consumed to form that film, with the remaining gas being exhausted to the atmosphere. Efforts to capture and recycle the excess $SF_6$ are difficult and expensive due to its very low concentrations in the high volumes of exhaust stream. Efficient thermal oxidizing equipment would be required to remove the $SF_6$ from the exhaust stream, adding significantly to production costs. Product costs can also be considerable, as $SF_6$ is the most expensive commercially used reactive cover gas.

However, perhaps the greatest concern with $SF_6$ is its very significant global warming potential (3200 year atmospheric lifetime, and about 22,200 times the global warming potential of carbon dioxide). At the December 1997 Kyoto Summit in Japan, representatives from 160 countries drafted a legally binding agreement containing limits for greenhouse gas emissions. The agreement covers six gases, including $SF_6$, and includes a commitment to lower the total emissions of these gases by the year 2010 to levels 5.2% below their total emissions in 1990. UNEP (United Nations Environment Programme), Kyoto Protocol to the United Nations Framework Convention on Climate Change, Nairobi, Kenya, 1997.

As no new replacement for $SF_6$ is yet commercially available, efforts are underway to reinvigorate $SO_2$, as $SO_2$ has essentially no global warming potential (despite its other considerable drawbacks). See H. Gjestland, P. Bakke, H. Westengen, and D. Magers, Gas protection of molten magnesium alloys: $SO_2$ as a replacement for $SF_6$. Presented at conference on Metallurgie du Magnesium et Recherche d''Allegement dans I''Industrie des Transports, International Magnesium Association (IMA) and Pole de Recherche et de Devleoppment Industriel du Magnesium (PREDIMAG) Clermond-Ferrand, France, October 1996.

The data in TABLE 1 summarize selected safety and environmental limitations of compounds currently known to be useful in the protection of molten magnesium. Numbers followed by an asterisk (*) are particularly problematic with regard to safety and/or environmental effects.

TABLE 1

| Compound | Exposure Guideline[1] | Atmospheric Lifetime[3] (yrs) | Global Warming Potential- GWP[3] (100 yr ITH) | Ozone Depletion Potential- ODP[3] (CFC-11 = 1) |
|---|---|---|---|---|
| $SO_2$ | 2 ppmv* | | | |
| $BF_3$ | 1 ppmv* | | | |
| $NF_3$ | 10 ppmv* | 740 | 10800* | |
| $SiF_4$ | 2.5 mg/m³ as F* | | | |
| $PF_5$ | 2.5 mg/m³ as F* | | | |
| $SF_6$ | 1000 ppmv | 3200 | 22200* | |
| $SO_2F_2$ | 5 ppmv* | | | |
| $(CClF_2)_2$ | 1000 ppmv | 300 | 9800* | 0.85* |
| HF | 3 ppmv ceiling* | | | |
| $NH_4F$ | 2.5 mg/m³ as F* | | | |
| $NH_4PF_6$ | corrosive, causes burns[2]* | | | |
| $CF_4$ | Moderately toxic by inhalation | 50000* | 5700* | |
| $CHClF_2$ | 1000 ppmv | 11.8 | 1900* | 0.055* |

[1]The Condensed Chemical Dictionary, edited by Gessner G. Hawley. New York, Van Nostrand Reinhold Co. (1981). Note: ppmv = parts per million by volume.
[2]Material Safety Data Sheet for ammonium hexafluorophosphate, Sigma-Aldrich Corporation, Milwaukee, WI.
[3]World Meterological Organization Global Research and Monitoring Project-Report No.44, "Scientific Assessment of Ozone Depletion: 1998," WMO (1999).

As each of these compounds presents either a significant safety or an environmental concern, the search continues to identify new reactive cover gases for protecting molten magnesium, aluminum, lithium, and alloys of such metals which are simultaneously effective, safe, environmentally acceptable, and cost-effective.

SUMMARY OF THE INVENTION

This invention relates in one aspect to a method for generating pollution credits while processing molten reactive metals and alloys of such metals, e.g., magnesium, aluminum, lithium, and alloys of one or more of such metals. Reactive metals are metals (and alloys) which are sensitive to destructive, vigorous oxidation in air. In brief summary, the invention provides a method for generating pollution credits comprising:

(a) treating molten reactive metal or alloy of such metal to protect said metal or alloy from reacting with oxygen in air by (1) providing molten metal or alloy and (2) exposing said metal or alloy to a gaseous mixture comprising a fluorocarbon selected from the group consisting of perfluoroketones, hydrofluoroketones, and mixtures thereof to yield protected metal or alloy having a protective film thereon; and (b) taking allocation of pollution credits.

In one embodiment, this invention employs a method for treating molten reactive metal or alloy to protect it from reacting with oxygen in air. The method comprises providing molten reactive metal or alloy and exposing it to a gaseous mixture comprising a fluorocarbon selected from the group consisting of perfluoroketones, hydrofluoroketones, and mixtures thereof. The gaseous mixture may further comprise a carrier gas. The carrier gas may be selected from the group consisting of air, carbon dioxide, argon, nitrogen and mixtures thereof.

One advantage of the present invention over the known art is that the Global Warming Potentials of perfluoroketones and hydrofluoroketones are quite low. Therefore, the present inventive process is more environmentally friendly. By employing the method for treating or protecting molten reactive metals or alloys which is described herein, processors who handle molten reactive metals or alloys will be able to produce unit quantities of such metals and alloys and parts containing such metals and alloys as before while generating much smaller quantities of materials exhibiting significant GWP contribution or other environmentally desirable effect.

DETAILED DESCRIPTION OF ILLUSTRATIVE EMBODIMENTS OF THE INVENTION

Fluorocarbons used in the present invention include perfluoroketones (PFKs), and hydrofluoroketones (HFKs) which incorporate limited amounts of hydrogen in their structures. These fluorocarbons can be effective as reactive cover gases to protect reactive molten reactive metals such as molten magnesium from ignition. As is the case with known fluorine-containing reactive cover gases, these fluorocarbons can react with the molten metal surface to produce a protective surface film, thus preventing ignition of the molten metal. For convenience, the following description refers to molten magnesium, but it should be understood that the invention is also applicable to other reactive molten metals and alloys, including aluminum, lithium and alloys of one or more of magnesium, aluminum or lithium.

For the protection of molten magnesium from ignition, fluorocarbons of the present invention are desirable alternatives to the most commonly used cover gas currently, $SF_6$. The fluorocarbons of the present invention are low GWP fluorocarbon alternatives to $SF_6$, i.e., the fluorocarbons of the present invention have measurably lower global warming potential relative to $SF_6$ (i.e., significantly less than 22,200) and are not significantly worse in atmospheric lifetime, ozone depletion potential, or toxicity properties.

Perfluorinated ketones (PFKs) useful in the present invention include ketones which are fully fluorinated, i.e., all of the hydrogen atoms in the carbon backbone have been replaced with fluorine atoms. The carbon backbone can be linear, branched, or cyclic, or combinations thereof, and will preferably have about 5 to about 9 carbon atoms. Representative examples of perfluorinated ketone compounds suitable for use in the processes and compositions of the invention include $CF_3CF_2C(O)CF(CF_3)_2$, $(CF_3)_2CFC(O)CF(CF_3)_2$, $CF_3(CF_2)_2C(O)CF(CF_3)_2$, $CF_3(CF_2)_3C(O)CF(CF_3)_2$, $CF_3(CF_2)_5C(O)CF_3$, $CF_3CF_2C(O)CF_2CF_2CF_3$, $CF_3C(O)CF(CF_3)_2$, perflurocyclohexanone, and mixtures thereof. In addition to demonstrating reactive cover gas performance, perfluorinated ketones can offer additional important benefits in safety of use and in environmental properties. For example, $CF_3CF_2C(O)CF(CF_3)_2$ has low acute toxicity, based on short-term inhalation tests with mice exposed for four hours at a concentration of 100,000 ppm in air. Also based on photolysis studies at 300 nm $CF_3CF_2C(O)CF(CF_3)_2$ has an estimated atmospheric lifetime of 5 days. Other perfluorinated ketones show similar absorbances and thus are expected to have similar atmospheric lifetimes. As a result of their rapid degradation in the lower atmosphere, the perfluorinated ketones have short atmospheric lifetimes and would not be expected to contribute significantly to global warming (i.e., low global warming potentials). Perfluorinated ketones which are straight chain or cyclic can be prepared as described in U.S. Pat. No. 5,466,877 (Moore et al.) which in turn can be derived from the fluorinated esters described in U.S. Pat. No. 5,399,718 (Costello et al.). Perfluorinated ketones that are branched can be prepared as described in U.S. Pat. No. 3,185,734 (Fawcett et al.). All of these patents are incorporated by reference in their entirety.

Hydrofluoroketones (HFKs) that are useful in the present invention include those ketones having only fluorine and hydrogen atoms attached to the carbon backbone. The carbon backbone can be linear, branched, or cyclic, or combinations thereof, and preferably will have about 4 to about 7 carbon atoms. Representative examples of hydrofluoroketone compounds suitable for use in the processes and compositions of this invention include: $HCF_2CF_2C(O)CF(CF_3)_2$, $CF_3C(O)CH_2C(O)CF_3$, $C_2H_5C(O)CF(CF_3)_2$, $CF_2CF_2C(O)CH_3$, $(CF_3)_2CFC(O)CH_3$, $CF_3CF_2C(O)CHF_2$, $CF_3CF_2C(O)CH_2F$, $CF_3CF_2C(O)CH_2CF_3$, $CF_3CF_2C(O)CH_2CH_3$, $CF_3CF_2C(O)CH_2CHF_2$, $CF_3CF_2C(O)CH_2CHF_2$, $CF_3CF_2C(O)CH_2CH_2F$, $CF_3CF_2C(O)CHFCH_3$, $CF_3CF_2C(O)CHFCHF_2$, $CF_3CF_2C(O)CHFCH_2F$, $CF_3CF_2C(O)CF_2CH_3$, $CF_3CF_2C(O)CF_2CHF_2$, $CF_3CF_2C(O)CF_2CH_2F$, $(CF_3)_2CFC(O)CHF_2$, $(CF_3)_2CFC(O)CH_2F$, $CF_3CF(CH_2F)C(O)CHF_2$, $CF_3CF(CH_2F)C(O)CH_2F$, and $CF_3CF(CH_2F)C(O)CF_3$. Some hydrofluoroketones can be prepared by reacting a fluorinated acid with a Grignard reagent such as an alkylmagnesium bromide in an aprotic solvent, as described in Japanese Patent No. 2,869,432. For example $CF_2CF_2C(O)CH_3$ can be prepared by reacting pentafluoropropionic acid with magnesium methyl bromide in dibutyl ether. Other hydrofluoroketones can be prepared by reacting a partially fluorinated acyl fluoride with hexafluoropropylene in an anhydrous environment in the presence of fluoride ion at elevated temperature, as described in U.S. patent application Ser. No. 09/619306 (herein incorporated by reference). For example, $HCF_2CF_2C(O)CF(CF_3)_2$ can be prepared by oxidizing tetrafluoropropanol with acidic dichromate, then reacting the resulting $HC_2H_4COOH$ with benzotrichloride to form $HC_2H_4C(O)Cl$, converting the acyl chloride to the acyl fluoride by reaction with anhydrous sodium fluoride, and then reacting the $HC_2H_4C(O)F$ with hexafluoropropylene under pressure.

The gaseous mixture that comprises a fluorocarbon selected from the group consisting of perfluoroketones and hydrofluoroketones further comprises a carrier gas or carrier gases. Some possible carrier gases include air, $CO_2$, argon, nitrogen and mixtures thereof. Preferably, the carrier gas that is used with the perfluroketones is dry air.

The gaseous mixture comprises a minor amount of the fluorocarbon and a major amount of the carrier gas. Preferably, the gaseous mixture consists of less than about 1% of the fluorocarbon and the balance carrier gas. More preferably, the gaseous mixture contains less than 0.5% by volume (most preferably less that 0.1% by volume) fluorocarbon, selected from the group consisting of perfluoroketones, hydrofluoroketones and mixtures thereof.

In order to keep the protective layer on the magnesium, the gaseous mixture is continuously, or nearly continuously, fed to the surface of the magnesium. Small breaks in the thin protective layer can then be healed without the possibility of such small breaks exposing molten magnesium to the air and initiating a fire.

A cover gas composition is of low toxicity both as it is applied to the molten magnesium and as it is emitted from the process in which it is used. Cover gases comprising low toxicity hydrofluoroketones and perfluoroketones, and mixtures thereof, will be safe mixtures as applied to magnesium. However, all fluorine containing cover gas composition produce measurable amounts of hydrogen fluoride upon contact with the molten magnesium due to some level of thermal degradation and reaction with magnesium at temperatures of 650 to 800° C. Hydrogen fluoride is corrosive and toxic and its concentration in the emitted gas should be minimized. A preferred cover gas composition will, therefore, produce minimal hydrogen fluoride. See Examples, below.

Atmospheric lifetimes and global warming potentials for several fluorocarbons used in accordance with this invention, along with compounds currently known to be useful in the protection of molten magnesium as comparative examples, are presented in TABLE 2.

TABLE 2

| Compound | Atmospheric Lifetime (years)[1] | Global Warming Potential (GWP) (100 year ITH)[1] | GWP relative to $SF_6$ |
|---|---|---|---|
| Hydrofluoroketone | | | |
| $HCF_2CF_2C(O)CF(CF_3)_2$ | ≤0.1[4] | ≤10[4] | 0.0005 |
| Perfluoroketone | | | |
| $C_2F_5C(O)CF(CF_3)_2$ | 0.02[2] | 1[2] | 0.00005 |
| Comparative Compounds: | | | |
| Hydrofluorocarbons | | | |
| $FCH_2CF_3$ | 13.6 | 1600 | 0.07 |
| $CF_3CHFCHFCF_2CF_3$ | 17.1 | 1700 | 0.08 |
| $CF_3CHFCF_3$ | 36.5 | 3800 | 0.17 |
| $HCF_2CF_3$ | 32.6 | 3800 | 0.17 |
| Segregated | | | |
| Hydrofluoroethers | | | |
| $C_4F_9OCH_3$ | 5.0 | 390 | 0.02 |
| $C_4F_9OC_2H_5$ | 0.8 | 55 | 0.002 |
| $C_3F_7CF(OC_2H_5)CF(CF_3)_2$ | 2.5[2] | 210[2] | 0.01 |
| Non-Segregated | | | |
| Hydrofluoroethers | | | |
| $HCF_2OCF_2CF_2OCF_2H$ | 7[3] | 1725[3] | 0.08 |
| $HCF_2OCF_2OC_2F_4OCF_2H$ | 7.1[3] | 1840[3] | 0.08 |
| Other Fluorochemicals | | | |
| $SF_6$ | 3200 | 22200 | 1.00 |
| $NF_3$ | 740 | 10800 | 0.49 |
| $CClF_2CClF_2$ | 300 | 9800 | 0.44 |
| $CF_4$ | 50000 | 5700 | 0.26 |
| $C_2F_6$ | 10,000 | 11,400 | 0.51 |

[1]World Meterological Organization Global Research and Monitoring Project-Report No. 44, "Scientific Assessment of Ozone Depletion: 1998, Vol. 2," Chapter 10, Table 10-8, pp. 10.27 to 10.28.
[2]Unpublished data, 3M Company, St. Paul, MN.
[3]Marchionni, G., et al., Journal of Fluorine Chemistry, 95, (1999), 41–50.
[4]Estimated, as described below.

The perfluoroketones and hydrofluoroketones used in accordance with the invention have much lower global warming potential (GWP) than the fluorocarbons known in the art such as $SF_6$, hydrofluorocarbons, and hydrofluoroethers. As used herein, "GWP" is a relative measure of the warming potential of a compound based on the structure of the compound. The GWP of a compound, as defined by the Intergovernmental Panel on Climate Change (IPCC) in 1990 and updated in Scientific Assessment of Ozone Depletion: 1998 (World Meteorological Organization, *Scientific Assessment of Ozone Depletion: 1998*, Global Ozone Research and Monitoring Project—Report No. 44, Geneva, 1999), is calculated as the warming due to the release of 1 kilogram of a compound relative to the warming due to the release of 1 kilogram of $CO_2$ over a specified integration time horizon (ITH).

$$GWP_x(t') = \frac{\int_0^{ITH} F_x C_{ox} e^{-t/\tau_x} dt}{\int_0^{ITH} F_{CO_2} C_{CO_2}(t) dt}$$

where F is the radiative forcing per unit mass of a compound (the change in the flux of radiation through the atmosphere due to the IR absorbance of that compound), C is the atmospheric concentration of a compound, $\tau$ is the atmospheric lifetime of a compound, t is time and x is the compound of interest.

The commonly accepted ITH is 100 years representing a compromise between short-term effects (20 years) and longer-term effects (500 years or longer). The concentration of an organic compound, x, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

Carbonyl compounds such as aldehydes and ketones have been shown to have measurable photolysis rates in the lower atmosphere resulting in very short atmospheric lifetimes. Compounds such as formaldehyde, acetaldehyde, propionaldehyde, isobutyraldehyde, n-butyraldehyde, acetone, 2-butanone, 2-pentanone and 3-pentanone have atmospheric lifetimes by photolysis ranging from 4 hours to 38 days (Martinez, R. D., et al., 1992, Atmospheric Environment, 26, 785–792, and Seinfeld, J. H. and Pandis, S. N., Atmospheric Chemistry and Physics, John Wiley & Sons, New York, p. 288, 1998). $CF_3CF_2C(O)CF(CF_3)_2$ has an atmospheric lifetime of approximately 5 days based on photolysis studies at 300 nm. Other perfluoroketones and hydrofluoroketones show similar absorbances near 300 nm and are expected to have similar atmospheric lifetimes.

The very short lifetimes of the perfluoroketones and hydrofluoroketones lead to very low GWPs. A measured IR cross-section was used to calculate the radiative forcing value for $CF_3CF_2C(O)CF(CF_3)_2$ using the method of Pinnock, et al. (*J. Geophys. Res.*, 100, 23227, 1995). Using this radiative forcing value and the 5-day atmospheric lifetime the GWP (100 year ITH) for $CF_3CF_2C(O)CF(CF_3)_2$ is 1. Assuming a maximum atmospheric lifetime of 38 days and infrared absorbance similar to that of $CF_3CF_2C(O)CF(CF_3)_2$ the GWP for $HCF_2CF_2C(O)CF(CF_3)_2$ is calculated to be 9. The perfluoroketones and hydrofluoroketones of the invention typically have a GWP less than about 10.

As a result of their rapid degradation in the lower atmosphere, the perfluoroketones and hydrofluoroketones have short lifetimes and would not be expected to contribute significantly to global warming. The low GWP of the perfluoroketones make them well suited for use as an environmentally preferred cover gas.

Also, the PFKs and HFKs of this invention can react more fully with molten magnesium than does $SF_6$. As a result less unreacted cover gas can be emitted to the atmosphere; less cover gas can be required to produce a comparably performing protective film; or both. Consequently, useful concentrations of the cover gas can be lowered, thus reducing the global warming impact. The full substitution of fluorocarbons of the present invention for $SF_6$ can be accomplished without increasing the risk to worker safety since these materials (PFKs, and HFKs) are of low toxicity, are nonflammable, and are generally very innocuous materials.

Substitution for $SF_6$ with a PFK, or HFK, alone or as a mixture thereof, can provide protection of molten magnesium in various processes, such as magnesium refining, alloying, formation of ingots or casting of parts. This substitution can be straightforward and can provide the same utility as a reactive cover gas that only $SF_6$ does currently. Surface films produced with the fluorocarbons of the present invention can be more stable to higher temperatures than those formed with $SO_2$, enabling work with higher melt temperatures (e.g., additional alloys, more complex casting parts). Improvements realized through the use of fluorocarbons of the present invention as reactive cover gases can include a significant reduction in the emission of a potent greenhouse gas (i.e., $SF_6$), a potential reduction in the amount of fluorine-containing reactive cover gas required to provide protection, and a reduction in total emissions. This substitution can be done without increasing risks for workers since the fluorocarbons of the present invention are all safe materials with which to work, have low toxicity, are nonflammable, and are not a detriment to production equipment.

The use of perfluoroketones, or hydrofluoroketones, or mixtures thereof, in a gaseous mixture demonstrate the ability to also put out fires that are already occurring on the surface of molten magnesium. Therefore, the gases also may be used to extinguish fires on molten magnesium.

As discussed above, the use of a gaseous mixture comprising a fluorocarbon selected from the group consisting of perfluoroketones, hydrofluoroketones, and mixtures thereof as a cover gas for handling molten magnesium instead of cover gases such as $SF_6$ provides an opportunity to reduce the emission of undesirable pollutants while producing similar, even increased amounts of magnesium. Accordingly, one can use the present invention to produce protected magnesium or other reactive metal or alloy and receive allocation of pollution credits.

In some applications, a magnesium producer can convert a facility which utilizes cover gas comprising $SF_6$ to instead utilize a gaseous mixture comprising a fluorocarbon selected from the group consisting of perfluoroketones, hydrofluoroketones, and mixtures thereof as a cover gas. Pollution credits may be allocated according to a function of: (1) how much protected reactive metal or alloy is processed or produced; (2) how much of a reduction in emissions or use of higher GWP cover gas (e.g., $SF_6$) is achieved; or (3) any other recognized system. As used herein, "allocation" of pollution credits is meant to include any system wherein credits are awarded, assigned, designated, or otherwise credited by any public or private agency for the processing of reactive metals or alloys.

EXAMPLES

The present invention is further illustrated, but is not meant to be limited by, the following examples. The standard test procedure for evaluating the efficiency of each test fluorocarbon cover gas is given below.

An approximately 3 kg sample of pure magnesium was placed in a cylindrical steel crucible having an 11.4 cm internal diameter and was heated to 680° C. Cover gas was continuously applied to the 410 cm² surface of the molten magnesium through a 10 cm diameter ring formed of 95 mm diameter stainless steel that was placed about 3 cm over the molten magnesium. The tubing was perforated on the side of the ring facing the molten magnesium so that the cover gas flowed directly over the molten magnesium. A square 20 cm×20 cm, 30 cm high stainless steel chamber with an internal volume of about 10.8 liters was fitted over the crucible to contain the cover gas. The top of the chamber was fitted with two 8.9 cm diameter quartz viewing ports and ports for a skimming tool and thermocouple. A cover gas inlet, two gas sampling ports and a door for adding fresh magnesium and for removing dross from the chamber were placed on the sides of the chamber.

A stream of the cover gas was pumped from the chamber into the flow cell of an FTIR spectrophotometer (Midac I2000 Gas Phase FTIR) with a mercury cadmium telluride (MCT) detector. Using Modified Extractive FTIR (EPA Method 320), the volumetric concentration of HF and the test cover gas (in ppmV) were measured continuously during experimentation. Once the mixtures had stabilized, concentrations were measured over a period of 5 to 10 minutes, average values of these concentrations were calculated, and those average values were used to make a relative comparison of the test cover gases.

In all cases, initial magnesium melting was done using a standard cover gas of 0.5% $SF_6$ in $CO_2$ at a flow rate of 5.9 L/min. The experimental gas mixture was then substituted for the standard cover gas mixture by utilizing a train of rotameters and valves. Dry air (having a −40° C. dew point) at a flow rate of 5.9 L/min was used to create the test cover gas by evaporating a flow of test fluid in it such that a volumetric concentration of 0.03 to 1 volume % fluorocarbon in air was produced.

During testing, the molten magnesium was observed for a period of about 20 to 30 minutes (equivalent to 10 to 15 chamber volumes exchanges of cover gas) to monitor any visible changes to the surface that would indicate the start of magnesium burning. The existing surface film was then removed by skimming the surface for about 3–5 minutes. The new surface film that formed was then observed for a period of at 15–30 minutes The concentration of the fluorocarbon component of the cover gas mixture was started at about 1% by volume in air and reduced sequentially in steps of ½ the previous concentration to a minimum fluorocarbon concentration of 0.03 to 0.06%.

Comparative Example C1

$C_4F_9OCH_3$ (methoxy nonafluorobutane), a hydrofluoroether, has been described as an effective fluorocarbon cover gas for molten magnesium in World Published Application WO 00/64614 (Example 5). In this comparative example, $C_4F_9OCH_3$ (available as NOVEC™ HFE-7100 Engineering Fluid from 3M Company, St. Paul, Minn.) was evaluated as a fluorocarbon cover gas at 1% and at decreasing volumetric concentrations in air. In all cases, the volumetric flow rate for the cover gas/air mixture was 5.9 L/min. At nominal concentrations of about 1, 0.5, 0.25 and 0.125% (corresponds to 10000, 5000, 2500 and 1250 ppmV, respectively), $C_4F_9OCH_3$ produced a thin flexible surface film on molten magnesium immediately after skimming so that no evidence of metal burning was observed. When the concentration of $C_4F_9OCH_3$ was reduced to 0.0625% (i.e., 625 ppmV), some evidence of burning was observed on the molten magnesium surface as white blooms, but no fire resulted. Exposure to fresh molten magnesium during skimming caused the HF concentration to remain essentially unchanged or to be increased at all volumetric concentrations of $C_4F_9OCH_3$ tested.

The HF concentrations measured at the various volumetric concentrations of $C_4F_9OCH_3$ tested are presented in TABLE 3.

TABLE 3

| Concentration of $C_4F_9OCH_3$ in Air Over Molten Magnesium (ppm by volume) | Concentration of Hydrogen Fluoride over Stable Surface Molten Magnesium Film (ppm by volume) | Concentration of Hydrogen Fluoride over Fresh Molten Magnesium Film (ppm by volume) |
|---|---|---|
| 8300 | 4500 | 4100 |
| 4100 | 2000 | 2200 |
| 2000 | 980 | 1000 |
| 800 | 590 | 480 |

The data in TABLE 3 show that significant hydrogen fluoride is produced at 800 ppm volumetric concentration of $C_4F_9OCH_3$ (i.e., 480–590 ppm HF), the minimum concentration required to protect molten magnesium from ignition.

Example 1

$CF_3CF_2C(O)CF(CF_3)_2$ (1,1,1,2,4,4,5,5,5-nonafluoro-2-trifluoromethyl-pentan-3-one), a perfluoroketone, was evaluated as a cover gas to protect molten magnesium from ignition using essentially the same procedure as described in Comparative Example C1 using $C_4F_9OCH_3$. The $CF_3CF_2C(O)CF(CF_3)_2$ was prepared and purified using the following procedures.

Into a clean dry 600 mL Parr reactor equipped with stirrer, heater and thermocouple were added 5.6 g (0.10 mol) of anhydrous potassium fluoride and 250 g of anhydrous diglyme (anhydrous diethylene glycol dimethyl ether, available from Sigma Aldrich Chemical Co.). The anhydrous potassium fluoride was spray dried, stored at 125° C. and ground shortly before use. The contents of the reactor were stirred while 21.0 g (0.13 mol) of $C_2F_5COF$ (approximately 95.0 percent purity) was added to the sealed reactor. The reactor and its contents were then heated, and when a temperature of 70° C. had been reached, a mixture of 147.3 g (0.98 mol) of $CF_2=CFCF_3$ (hexafluoropropylene) and 163.3 g (0.98 mol) of $C_2F_5COF$ was added over a 3.0 hour time period. During the addition of the hexafluoropropylene and the $C_2F_5COF$ mixture, the pressure was maintained at less than 95 psig (7500 torr). The pressure at the end of the hexafluoropropylene addition was 30 psig (2300 torr) and did not change over the 45-minute hold period. The reactor contents were allowed to cool and were one-plate distilled to obtain 307.1 g containing 90.6% $CF_3CF_2C(O)CF(CF_3)_2$ and 0.37% $C_6F_{12}$ (hexafluoropropylene dimer) as determined by gas chromatography. The crude fluorinated ketone was water-washed, distilled, and dried by contacting with silica gel to provide a fractionated fluorinated ketone of 99% purity and containing 0.4% hexafluoropropylene dimers.

A sample of fractionated $CF_3CF_2C(O)CF(CF_3)_2$ made according to the above-described procedure was purified of hexafluoropropylene dimers using the following procedure. Into a clean dry 600 mL Parr reactor equipped with stirrer, heater and thermocouple were added 61 g of acetic acid, 1.7 g of potassium permanganate, and 301 g of the above-described fractionated 1,1,1,2,4,4,5,5,5-nonafluoro-2-trifluoromethyl-pentan-3-one. The reactor was sealed and heated to 60° C., while stirring, reaching a pressure of 12 psig (1400 torr). After 75 minutes of stirring at 60° C., a liquid sample was taken using a dip tube, the sample was phase split and the lower phase was washed with water. The sample was analyzed using gas-liquid chromatography ("glc") and showed undetectable amounts of hexafluoropropylene dimers and small amounts of hexafluoropropylene trimers. A second sample was taken 60 minutes later and was treated similarly. The glc analysis of the second sample showed no detectable dimers or trimers. The reaction was stopped after 3.5 hours, and the purified ketone was phase split from the acetic acid and the lower phase was washed twice with water. 261 g of $CF_3CF_2C(O)CF(CF_3)_2$ was collected, having a purity greater than 99.6% by glc and containing no detectable hexafluoropropylene dimers or trimers.

The perfluorinated ketone, $CF_3CF_2C(O)CF(CF_3)_2$, was then evaluated as a fluorocarbon cover gas at 1% and at decreasing volumetric concentrations in air (i.e., at about 1.0, 0.5, 0.25, 0.12, 0.06 and 0.03% by volume; corresponds to 10000, 5000, 2500, 1250, 600 and 300 ppm, respectively). At all concentrations tested, $CF_3CF_2C(O)CF(CF_3)_2$ produced a thin flexible surface film on the molten magnesium during skimming and prevented metal ignition. The film visually appeared to be thinner and more elastic than the surface film produced in the initial molten magnesium protection using $SF_6$ as a cover gas and in Comparative Example C1 using $C_4F_9OCH_3$ as a cover gas. The silvery-gray film produced was stable and did not change appearance over at least 30 minutes. This is in contrast to the series using $C_4F_9OCH_3$, where evidence of metal burning was noted when the cover gas concentration was reduced to about 625 ppm.

The HF concentrations measured at the various volumetric concentrations of $CF_3CF_2C(O)(CF_3)_2$ tested are, presented in TABLE 4.

TABLE 4

| Concentration of $CF_3CF_2C(O)CF(CF_3)_2$ in Air over Molten Magnesium (ppm by volume) | Concentration of Hydrogen Fluoride over Stable Surface Molten Magnesium Film (ppm by volume) | Concentration of Hydrogen Fluoride over Fresh Molten Magnesium Film (ppm by volume) |
|---|---|---|
| 10400 | 420 | 670 |
| 4800 | 470 | 775 |
| 2400 | 360 | 640 |
| 1200 | 280 | 370 |
| 560 | 180 | 120 |
| 480 | 120 | 100 |
| 280 | 40 | 40 |

The data in TABLE 2 show that, at equal volumetric concentrations, significant less hydrogen flouride is produced using $CF_3CF_2C(O)CF(CF_3)_2$ compared to $C_4F_9OCH_3$ as a cover gas. For example, at 2000 ppm $C_4F_9OCH_3$, 980 ppm of HF was produced over the stable surface film and 1000 ppm of HF was produced over the fresh molten film. In contrast, at 2400 ppm $CF_3CF_2C(O)CF(CF_3)_2$ (a slightly higher fluorocarbon concentration), only 360 ppm of HF was produced over the stable surface film and 640 ppm of HF was produced over the fresh molten film.

In summary, the perfluorinated ketone outperformed the hydrofluoroether as a cover gas for molten magnesium (i.e. protected the molten magnesium at lower concentrations) and also generated less hydrogen fluoride as a degradation product upon exposure to the molten metal surface.

Various modifications and alterations of this invention will become apparent to those skilled in the art without departing from the scope of this invention. Accordingly, it is to be understood that this invention is not to be limited to the illustrative embodiments set forth herein, but is to be controlled by the limitations set forth in the following claims and any equivalents thereof.

What is claimed is:

1. A method for generating pollution credits comprising (a) treating molten reactive metal or alloy to protect said molten metal or alloy from reacting with oxygen in air by (1) providing molten metal or alloy and (2) exposing said molten metal or alloy to a gaseous mixture comprising a fluorocarbon selected from the group consisting of perfluoroketones, hydrofluoroketones, and mixtures thereof to yield protected metal or alloy having a protective film thereon and (b) taking allocation of pollution credits.

2. The method of claim 1 wherein said protected molten metal or alloy is selected from the group consisting of molten metal or alloy and solid metal or alloy.

3. The method of claim 1 wherein said pollution credits are allocated according to a function of how much protected metal or alloy is processed.

4. The method of claim 1 further comprising converting means for handling molten reactive metal or alloy employing $SF_6$ as a cover gas to means for handling molten reactive metal or alloy employing a gaseous mixture comprising a fluorocarbon selected from the group consisting of perfluoroketones, hydrofluoroketones, and mixtures thereof.

5. The method of claim 4 wherein said pollution credits are allocated according to a function of said reduction in $SF_6$ usage.

6. The method of claim 1 wherein said fluorocarbon is a hydrofluoroketone that is selected from the group consisting of $HCF_2CF_2C(O)CF(CF_3)_2$, $CF_3C(O)CH_2C(O)CF_3$, $C_2H_5C(O)CF(CF_3)_2$, $CF_2CF_2C(O)CH_3$, $(CF_3)_2CFC(O)CH_3$, $CF_3CF_2C(O)CHF_2$, $CF_3CF_2C(O)CH_2F$, $CF_3CF_2C(O)CH_2CF_3$, $CF_3CF_2C(O)CH_2CH_3$, $CF_3CF_2C(O)CH_2CHF_2$, $CF_3CF_2C(O)CH_2CHF_2$, $CF_3CF_2C(O)CH_2CH_2F$, $CF_3CF_2C(O)CHFCH_3$, $CF_3CF_2C(O)CHFCHF_2$, $CF_3CF_2C(O)CHFCH_2F$, $CF_3CF_2C(O)CF_2CH_3$, $CF_3CF_2C(O)CF_2CHF_2$, $CF_3CF_2C(O)CF_2CH_2F$, $(CF_3)_2CFC(O)CHF_2$, $(CF_3)_2CFC(O)CH_2F$, $CF_3CF(CH_2F)C(O)CHF_2$, $CF_3CF(CH_2F)C(O)CH_2F$, $CF_3CF(CH_2F)C(O)CF_3$, and mixtures thereof.

7. The method of claim 1 wherein the gaseous mixture further comprises a carrier gas.

8. The method of claim 7 wherein said carrier gas is selected from the group consisting of air, $CO_2$, argon, nitrogen, and mixtures thereof.

9. The method of claim 1 wherein said perfluoroketone is selected from the group consisting of $CF_3CF_2C(O)CF(CF_3)_2$, $(CF_3)_2CFC(O)CF(CF_3)_2$, $CF_3(CF_2)_2C(O)CF(CF_3)_2$, $CF_3(CF_2)_3C(O)CF(CF_3)_2$, $CF_3(CF_2)_5C(O)CF_3$, $CF_3CF_2C(O)CF_2CF_2CF_3$, $CF_3C(O)CF(CF_3)_2$, perfluorocyclohexanone, and mixtures thereof.

* * * * *

UNITED STATES PATENT AND TRADEMARK OFFICE
CERTIFICATE OF CORRECTION

PATENT NO. : 6,780,220 B2
DATED : August 24, 2004
INVENTOR(S) : Milbrath, Dean S.

It is certified that error appears in the above-identified patent and that said Letters Patent is hereby corrected as shown below:

Title page,
Item [56], References Cited, OTHER PUBLICATIONS,
"The Montreal" reference, "delete "Protoool" and insert -- Protocol --, therefore;
"S.O. Andersen" reference, after "Halons" insert -- , --;

Column 2,
Line 64, delete "et. al." and insert -- et al. --; therefore;

Column 5,
Line 61, delete "perflurocyclohexanone" and insert -- perfluorocyclohexanone --, therefore;

Column 10,
Line 39, after "minutes" insert -- . --;

Column 12,
Line 24, after "the" insert -- test --;
Line 29, delete "$CF_3CF_2C(O)(CF_3)_2$" and insert -- $CF_3CF_2C(O)CF(CF_3)_2$ --, therefore and after "are" delete ",";
Line 47, delete "flouride" and insert -- fluoride --, therefore.

Signed and Sealed this

Tenth Day of May, 2005

JON W. DUDAS
*Director of the United States Patent and Trademark Office*